United States Patent [19]

Ottersbach et al.

[11] Patent Number: 5,967,714
[45] Date of Patent: Oct. 19, 1999

[54] PROCESS FOR THE PREPARATION OF ANTIMICROBIAL PLASTICS

[75] Inventors: Peter Ottersbach, Windeck; Frank Hill, deceased, late of Mettmann, by Hella Luise Hill, heiress, Henning Hinrich Hill, heir; by Friedrich Frank Hill, heir, Waldsee; by Regina Luise Hill, heiress, Speyer; Christine Anders, Haltern, all of Germany

[73] Assignee: Huels Aktiengesellschaft, Marl, Germany

[21] Appl. No.: 09/035,993

[22] Filed: Mar. 6, 1998

[30] Foreign Application Priority Data

Mar. 6, 1997 [DE] Germany .............. 197 09 075

[51] Int. Cl.⁶ .............. B05D 3/06; B05D 3/08; B05D 3/10; B05D 7/00

[52] U.S. Cl. .............. 408/424.2; 424/411; 424/422; 424/447; 427/2.1; 427/2.31; 427/302; 427/316; 427/322; 427/508; 427/533; 427/536; 427/538; 427/539; 427/540; 427/551; 427/558; 604/265; 428/412; 428/476.3; 428/483; 428/500

[58] Field of Search .............. 427/2.24, 2.28, 427/2.3, 2.1, 2.31, 533, 557, 558, 385.5, 322, 302, 314, 551, 508, 316, 536, 538, 539, 540; 424/411, 422, 447; 604/265; 428/424.2, 422, 412, 451, 475.8, 476.3, 483, 494, 500, 518, 515

[56] References Cited

U.S. PATENT DOCUMENTS

| | | | |
|---|---|---|---|
| 3,592,805 | 7/1971 | Szabo et al. . | |
| 3,632,387 | 1/1972 | Sutherland | 427/307 |
| 3,829,564 | 8/1974 | Merry et al. | 424/78 |
| 3,855,040 | 12/1974 | Malofsky | 156/310 |
| 3,861,396 | 1/1975 | Vaillancourt et al. . | |
| 4,310,600 | 1/1982 | Cross | 427/412.5 |
| 4,515,910 | 5/1985 | Rawls et al. | 523/115 |
| 4,532,269 | 7/1985 | Gitlitz et al. | 523/122 |
| 4,772,518 | 9/1988 | Marthe | 427/411 |
| 5,002,582 | 3/1991 | Guire et al. | 427/2.24 |
| 5,051,312 | 9/1991 | Allmer | 428/458 |
| 5,053,048 | 10/1991 | Pinchuk | 427/2.1 |
| 5,132,108 | 7/1992 | Narayanan et al. | 427/2.1 |
| 5,154,920 | 10/1992 | Flesher et al. | 514/643 |
| 5,240,747 | 8/1993 | Matsuda et al. | 427/2.1 |
| 5,246,451 | 9/1993 | Trescony et al. | 427/2.25 |
| 5,272,012 | 12/1993 | Opolski | 427/2.1 |
| 5,744,243 | 4/1998 | Li et al. | 428/447 |
| 5,800,545 | 9/1998 | Yamada et al. | 427/2.1 |

FOREIGN PATENT DOCUMENTS

| | | |
|---|---|---|
| 0 204 312 | 12/1986 | European Pat. Off. . |
| 0 290 676 | 11/1988 | European Pat. Off. . |
| 2 707 288 | 1/1995 | France . |
| WO 91/12282 | 8/1991 | WIPO . |

*Primary Examiner*—Diana Dudash
*Attorney, Agent, or Firm*—Oblon, Spivak, McClelland, Maier & Neustadt, P.C.

[57] ABSTRACT

Antimicrobial activity is imparted to the surface(s) of an apparatus or article by a method, comprising:

copolymerizing tertbutylaminoethyl methacrylate with at least one other aliphatically unsaturated monomer in the presence of said apparatus or article by which adhesion of the copolymer to said surface(s) is achieved. In an embodiment of the invention, adhesion of the polymer coating on the apparatus or article occurs by graft copolymerization.

16 Claims, No Drawings

PROCESS FOR THE PREPARATION OF ANTIMICROBIAL PLASTICS

BACKGROUND OF THE INVENTION

Field of the Invention

The present invention relates to antimicrobial polymers prepared by copolymerization of tert-butylaminoethyl methacrylate with one or more aliphatically unsaturated monomers, a process for their preparation and their use. More particularly, the invention relates to antimicrobial polymers prepared by graft copolymerization of tert-butylaminoethyl methacrylate with one or more aliphatically unsaturated monomers on a substrate, a process for their preparation and their use.

Colonization and spread of bacteria on surfaces of pipelines, containers or packaging are highly undesirable. Layers of slime often form, which allow the microbe populations to rise to extreme levels, lastingly impairing the quality of water, drinks and foodstuffs, and can even lead to decay of the goods and damage to the health of consumers.

Bacteria are to be kept away from all areas of life where hygiene is of importance. Since textiles directly contact the body, and in particular the genital area, and are used for the care of the sick and elderly, textiles should be freed of bacteria. Bacteria should also be kept away from the surfaces of furniture and equipment in nursing wards, in particular in the intensive care and infant care sector, in hospitals, especially in rooms for medical operations, and in isolation wards for critical cases of infection, as well as in toilets.

Equipment and surfaces of furniture and textiles are currently treated to ward against bacteria as required or also preventively with chemicals or solutions and mixtures thereof which act as disinfectants, such having a more or less broad and massive antimicrobial action. Such chemical compositions have a non-specific action, are often themselves toxic or irritating, or form degradation products which are unacceptable to health. Intolerances are often also found in appropriately sensitized persons.

Another procedure which is used to inhibit the spread of bacteria on surfaces is to incorporate antimicrobially active substances into a matrix.

Tert-butylaminoethyl methacrylate is a commercially available monomer of methacrylate chemistry and is employed in particular as a hydrophilic monomer in copolymerizations. Thus, EP 0 290 676 describes the use of various polyacrylates and polymethacrylates as a matrix for immobilization of bactericidal quaternary ammonium compounds.

U.S. Pat. No. 3,592,805 discloses the preparation of systemic fungicides in which perhalogenated acetone derivatives are reacted with methacrylate esters, such as, for example, tert-butylaminoethyl methacrylate.

U.S. Pat. No. 4,515,910 describes the use of polymers of hydrogen fluoride salts of aminomethacrylates in dental medicine. The hydrogen fluoride bonded in the polymers emerges slowly from the polymer matrix and is said to have actions against caries.

In another technical field, U.S. Pat. No. 4,532,269 discloses a terpolymer of butyl methacrylate, tributyltin methacrylate and tert-butylaminoethyl methacrylate. This polymer is used as an antimicrobial paint for ships, the hydrophilic tert-butylaminoethyl methacrylate promoting slow erosion of the polymer and in this way liberating the highly toxic tributyltin methacrylate as an antimicrobially active compound.

In these applications, the copolymer prepared with aminomethacrylates is only a matrix or carrier substance for the added microbicidal active compounds, which can diffuse or migrate out of the carrier. Polymers of this type lose their action at a greater or lesser speed when the necessary "minimum inhibitory concentration" (MIC) is no longer achieved on the surface.

EP 0 204 312 describes a process for the preparation of antimicrobially treated acrylonitrile fibers. The antimicrobial action is based on a protonated amine as a comonomer unit, dimethylaminoethyl methacrylate and tertbutylaminoethyl methacrylate, inter alia, being used as protonated species. However, the antimicrobial action of pronated surfaces is severely reduced after loss of the H⊕ ions. A need, therefore, continues to exist for an improved method of providing surfaces with anti-bacterial properties.

SUMMARY OF THE INVENTION

Accordingly, one object of the present invention is to provide materials which have antimicrobial properties, which contain no active compounds which can be washed out, and in which the antimicrobial action is pH-independent.

Briefly, this object and other objects of the present invention as hereinafter will become more readily apparent can be attained by a method of imparting antimicrobial activity to the surface(s) of an apparatus or article, by copolymerizing tertbutylaminoethyl methacrylate with at least one other aliphatically unsaturated monomer in the presence of said apparatus or article by which adhesion of the copolymer to said surface(s) is achieved.

An aspect of the invention is a process for the preparation of antimicrobial polymers, which comprises subjecting tert-butylaminoethyl methacrylate to grafting copolymerization with one or more aliphatically unsaturated monomers on a substrate.

DETAILED DESCRIPTION OF THE PREFERRED EMBODIMENTS

It has now been found, surprisingly, that polymers which have a surface which is permanently microbicidal, is not attacked by solvents and physical stresses and shows no migration are obtained by copolymerization of tertbutylaminoethyl methacrylate with one or more other aliphatically unsaturated monomers or by grafting copolymerization of tert-butylaminoethyl methacrylate with one or more aliphatically unsaturated monomers on a substrate. It is not necessary to provide the polymer with biocidally active compounds.

The copolymerization of tert-butylaminoethyl methacrylate and one or more other aliphatically unsaturated monomers can be carried out by graft copolymerization on a substrate and is possible with the microbicidal action being largely retained. All aliphatically unsaturated monomers are suitable for this, such as, for example, acrylates and methacrylates of the formula:

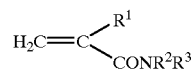

wherein $R^1$ is hydrogen or methyl, $R^2$ is hydrogen, a metal atom or a branched or unbranched aliphatic, cycloaliphatic, heterocyclic or aromatic hydrocarbon group having up to 20 carbon atoms or a branched or unbranched aliphatic, cycloaliphatic, heterocyclic or aromatic hydrocarbon chain having up to 20 carbon atoms, which is derivatized by carboxyl groups, carboxylate groups, sulfonate groups, alkylamino groups, alkoxy groups, halogens, hydroxyl groups, amino groups, dialkyl amino groups, phosphate groups, phosphonate groups, sulfate groups, carboxamido groups, sulfonamido groups, phosphonamido groups or combinations of these groupings. $R^3$ can be hydrogen or identical to $R^2$.

It is furthermore possible to employ vinyl compounds of the formula:

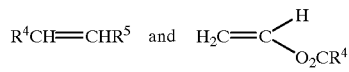

and maleic and fumaric acid derivatives of the formula

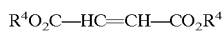

in which $R^4$ can be hydrogen, an aromatic radical or a methyl group or can be identical to $R^2$.

$R^5$ can be hydrogen, a methyl group or a hydroxyl group, and can be identical to $R^2$, or can be an ether of the composition $OR^2$.

Suitable substrate materials include all polymeric plastics, such as, for example, polyurethanes, polyamides, polyesters, polyethers, polyether-block amides, polystyrene, polyvinyl chloride, polycarbonates, polyorganosiloxanes, polyolefins, polysulfones, polyisoprene, polychloroprene, polytetrafluoroethylene (PTFE), corresponding copolymers and blends, as well as natural and synthetic rubbers, with or without radiation-sensitive groups. The process of the invention can also be applied to surfaces of metal, glass or wooden bodies which are painted or are otherwise coated with plastic.

The substrates' surfaces can be activated by a number of methods before the grafting copolymerization. They are expediently freed from oils, greases or other impurities beforehand in a known manner by means of a solvent.

The standard polymers can be activated by UV radiation. A suitable source of radiation is, for example, a UV-Excimer apparatus HERAEUS Noblelight, Hanau, Germany. However, mercury vapor lamps are also suitable for activation of the substrate if they emit considerable proportions of the radiation in the ranges mentioned. The exposure time generally ranges from 0.1 second to 20 minutes, preferably 1 second to 10 minutes.

The activation of the standard polymers with UV radiation can furthermore be carried out with an additional photosensitizer. Suitable such photosensitizers include, for example, benzophenone, as such are applied to the surface of the substrate and irradiated. In this context, irradiation can be conducted with a mercury vapor lamp using exposure times of 0.1 second to 20 minutes, preferably 1 second to 10 minutes.

According to the invention, the activation can also be achieved by a high frequency or microwave plasma (Hexagon, Technics Plasma, 85551 Kirchheim, Germany) in air or a nitrogen or argon atmosphere. The exposure times generally range from 30 seconds to 30 minutes, preferably 2 to 10 minutes.

The energy output of laboratory apparatus is between 100 and 500 W, preferably between 200 and 300 W. Corona apparatus (SOFTAL, Hamburg, Germany) can furthermore be used for the activation. In this case, the exposure times are, as a rule, 1–10 minutes, preferably 1–60 seconds.

Activation by electron beams or γ rays, for example, from a cobalt-60 source, and ozonization allows short exposure times which generally range from 0.1–60 seconds.

The flaming of surfaces likewise leads to activation of the surfaces. Suitable apparatus, in particular those having a barrier flame front, can be constructed in a simple manner or obtained, for example, from ARCOTEC, 7129 Mönsheim, Germany. The apparatus can employ hydrocarbons or hydrogen as the combustible gas. In all cases, harmful overheating of the substrate must be avoided, which is easily achieved by intimate contact with a cooled metal surface on the substrate surface facing away from the flaming side. Activation by flaming is accordingly limited to relatively thin, flat substrates. The exposure times generally range from 0.1 second to 1 minute, preferably 0.5–2 seconds, The flames without exception are non-luminant and the distances between the substrate surfaces and the outer flame front range from 0.2–5 cm, preferably 0.5–2 cm.

The substrate surfaces activated in this way are coated with tert-butylamino-ethyl methacrylate and one or more other aliphatically unsaturated monomers, if appropriate in solution, by known methods such as by dipping, spraying or brushing. Suitable solvents have proved to be water and water/ethanol mixtures, although other solvents can also be used if they have a sufficient dissolving power for the monomers and wet the substrate surfaces thoroughly. Solutions having monomer contents of 1–10% by weight, for example about 5% by weight, have proved suitable in practice and in general give continuous coatings which cover the substrate surface and have coating thicknesses which can be more than 0.1 μm in one pass.

The grafting copolymerization of the monomers applied to the activated surfaces is expediently effected by short wavelength radiation in the visible range or in the long wavelength segment of the UV range of electromagnetic radiation. The radiation of a UV-Excimer of wavelengths 250–500 mm, preferably 290–320 mm, for example, is particularly suitable. Mercury vapor lamps are also suitable here if they emit considerable amounts of radiation in the ranges mentioned. The exposure times generally range from 10 seconds to 30 minutes, preferably 2–15 minutes.

Copolymers with tert-butylaminoethyl methacrylate as the comonomer unit also show intrinsic microbicidal properties without grafting to a substrate surface.

One embodiment of the present invention comprises a procedure in which the copolymerization of tert-butylaminoethyl methacrylate and one or more other aliphatically unsaturated monomers can be carried out on a substrate.

The present polymers of tert-butylaminoethyl methacrylate and at least one other aliphatically unsaturated monomers can be applied to the substrate in solution.

Suitable solvents include, for example, water, ethanol, methanol, methyl ethyl ketone, diethyl ether, dioxane, hexane, heptane, benzene, toluene, chloroform, methylene chloride, tetrahydrofuran and acetonitrile.

The solution of the polymers according to the invention is applied to the standard polymers, for example, by dipping, spraying or painting.

If the present polymer is produced directly on the substrate surface without grafting, suitable initiators are added in order to promote polymerization. Initiators which can be used include, inter alia, azonitriles, alkyl peroxides, hydroperoxides, acyl peroxides, peroxoketones, peresters, peroxocarbonates, peroxodisulfate, persulfate and all the customary photoinitiators, such as, for example, acetophenones and benzophenone.

The initiation of the polymerization can be carried out by means of heat or by electromagnetic radiation, such as, for example, UV light or γ-radiation.

The products coated with the present polymers can be medical articles or hygiene articles. Products of the invention which are obtained by grafting copolymerization can likewise be medical articles or hygiene articles.

The products coated with the present polymers can be used for the production of medical articles, such as, for example, catheters, blood bags, drainages, guide wires and surgical instruments, as well as for the production of hygiene articles, such as, for example, toothbrushes, toilet seats, combs and packaging materials.

Having generally described this invention, a further understanding can be obtained by reference to certain specific examples which are provided herein for purposes of illustration only and are not intended to be limiting unless otherwise specified.

EXAMPLE 1

A 19.2 g amount of tert-butylaminoethyl methacrylate, 2.6 g of methyl methacrylate and 150 ml of tetrahydrofuran is heated to 60° C. under an inert gas. When the temperature is reached, 0.33 g of azobisisobutyronitrile, dissolved in 10 ml of tetrahydrofuran, is added. At the end of 24 hours, the reaction is ended by stirring the mixture into 1 liter of a water/ice mixture. The reaction product is filtered and washed with 300 ml of n-hexane. The product is then distributed over several Soxhlets and extracted with water for 24 hours, and is then dried at 50° C. in vacuo for 12 hours.

EXAMPLE 2

A 4 g amount of copolymer from Example 1 is dissolved in 40 ml of tetrahydrofuran. A polyamide 12 film is immersed in this solution for 5 seconds, removed from the solution for 10 seconds and them immersed again for 5 seconds, so that a uniform film of the copolymer on the polyamide film has formed after subsequent drying at room temperature under normal pressure. The film is then dried at 50° C. in vacuo for 24 hours. The film is subsequently extracted in water at 30° C. five times for 6 hours and then dried at 50° C. for 12 hours.

EXAMPLE 3

A 4 g amount of copolymer from Example 1 is dissolved in 40 ml of tetrahydrofuran. A polyvinyl chloride film is immersed in this solution for 2 seconds, removed from the solution for 10 seconds and then immersed again for 2 seconds, so that a uniform film of the copolymer has formed on the polyvinyl chloride film after subsequent drying at room temperature under normal pressure. The film is then dried at 50° C. in vacuo for 24 hours. The film is subsequently extracted in water at 30° C. five times for 6 hours and then dried at 50° C. for 12 hours.

EXAMPLE 4

A polyamide 12 film is exposed to the 172 nm radiation of an Excimer radiation source manufactured by Heraeus for 2 minutes under a pressure of 1 mbar. The film activated in this way is laid and fixed in an irradiation reactor under an inert gas. The film is then covered with a layer of 20 ml of a mixture of 3 g of tert-butylaminoethyl methacrylate, 2 g of methyl methacrylate and 95 g of methanol in a countercurrent flow of inert gas. The irradiation chamber is closed and placed a distance of 10 cm underneath an Excimer radiation unit manufactured by Heraeus, which has an emission of wavelength 308 nm. The irradiation is started, and the exposure time is 15 minutes. The film is removed and rinsed with 30 ml of methanol. The film is then dried at 50° C. in vacuo for 12 hours. The film is subsequently extracted in water at 30° C. five times for 6 hours, and then dried at 50° C. for 12 hours.

Measurement of bactericidal action:

The bactericidal action of coated plastics was measured as follows:

A 100 μl amount of a cell suspension of Klebsiella pneumoniae were placed on a piece of film 2×2 cm in size. The bacteria were suspended in PBS buffer (phosphate-buffered saline); the cell concentration was $10^5$ cells per ml of buffer solution. This drop was incubated for up to 3 hours. In order to prevent any drying of the applied drop, the piece of film was laid in a polystyrene Petri dish wetted with 1 ml of water. After the end of the contact time, the 100 pl were taken up with an Eppendorf tip and diluted in 1.9 ml of sterile PBS. A 0.2 ml amount of this solution was plated out on nutrient agar. The rate of inactivation was calculated from the number of colonies which had grown.

Checking the resistance of the coatings:

Before the measurement of the bactericidal action, the coated films were subjected to the following pretreatments:

A: Washing in boiling water for 10 minutes

B: washing in 96% strength ethanolic solution for 10 minutes

C: Washing in warm water at 25° C. under ultrasonic treatment for 10 minutes

D: No pretreatment

The results of the measurements, taking into account the particular pretreatment, are listed in Table 1.

TABLE 1

| | Rate of inactivation | | | |
|---|---|---|---|---|
| Example: | A | B | C | D |
| 2 | 2% | <10% | 51% | 99.9% |
| 3 | 2% | <10% | 50% | 99.9% |
| 4 | 99.9% | 99.9% | 99.9% | 99.9% |

After thermal, chemical or mechanical pretreatment, the antimicrobial layers produced by grafting of a substrate surface continue to show virtually complete inactivation of the bacteria applied. The physically adhered layers are less stable than the pretreatments of methods A, B and C.

In addition to the microbicidal activity against cells of Klebsiella pneumoniae which has been described above, all the coated films also showed a microbicidal action against cells of *Pseudomonas aeruginosa, Staphylococcus aureus, Escherichia coli, Rhizopus oryzae, Candida tropicalis* and *Tetrahymena pyriformis*. The rate of inactivation after treatment method D was also more than 99% in these cases.

The disclosure of priority German Application No. 197 09 075.3 filed Mar. 6, 1997 is hereby incorporated into the disclosure of the application.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A method of imparting antimicrobial activity to a polymer-containing surface(s) of an apparatus or article, comprising:

forming a copolymer by graft copolymerizing tertbutylaminoethyl methacrylate with at least one other aliphatically unsaturated monomer in the presence of said apparatus or article by which adhesion of the copolymer to said surface(s) is achieved.

2. The method of claim 1, wherein the surface(s) is activated before the grafting polymerization.

3. The method of claim 2, wherein the activation of the surfaces(s) is carried out by UV radiation with or without an additional photosensitizer, plasma treatment, corona treatment, flaming, ozonization, electrical discharge or γ-radiation.

4. The method of claim 1, wherein said apparatus provided with antibacterial activity is a medical article.

5. The method of claim 1, wherein said apparatus provided with antimicrobial activity is an article that comes into contact with human body surfaces.

6. The method as claimed in claim 1, wherein the apparatus or article is manufactured of polyurethane, polyamide, polyester, polyether, polyether-block amides, polystyrene, polyvinyl chloride, polycarbonate, polyorganosiloxanes, polyolefins, polysulfones, polyisoprene, polychloroprene, polytetrafluoroethylene, blends of these polymers or natural or synthetic rubber.

7. The method as claimed in claim 2, wherein said surface(s) of the apparatus or article is activated by exposure to UV radiation.

8. The method as claimed in claim 7, wherein said activation occurs in the presence of a photosensitizer.

9. The method as claimed in claim 2, wherein said activation is effected by subjecting said surface(s) to a high frequency or microwave plasma.

10. The method as claimed in claim 2, wherein said activation is effected by subjecting said surface(s) to electron beam or γ-radiation or by ozonization.

11. The method as claimed in claim 2, further comprising applying a solution of t-butylaminoethyl methacrylate to said surface(s), and effecting graft polymerization by exposure of the applied solution to radiation.

12. The method as claimed in claim 11, wherein the t-butylaminoethyl methacrylate concentration in solution ranges from 1% to 10% by weight.

13. The method as claimed in claim 12, wherein said radiation is of 250–500 nm wavelength.

14. A coated article comprising an antimicrobial polymer prepared by graft copolymerizing t-butylaminoethyl methacrylate with one or more aliphatically unsaturated monomers on a polymer-containing substrate.

15. The coated article as claimed in claim 14, which is prepared by activation of the substrate before the graft polymerization.

16. The coated article as claimed in claim 15, which is prepared by activation of the substrate by UV radiation with or without an additional photosensitizer, plasma treatment, corona treatment, flaming, ozonization, electrical discharge or γ-radiation.

* * * * *